US008560360B2

(12) United States Patent  (10) Patent No.: US 8,560,360 B2
Olsen et al.  (45) Date of Patent: Oct. 15, 2013

(54) METHOD, SYSTEM AND COMPUTER PROGRAM FOR AUTOMATED INTERPRETATION OF MEASUREMENTS IN RESPONSE TO STIMULI

(75) Inventors: Birger Jan Olsen, Kobenhavn Ø (DK); Jens Nicolai Krarup, London (CA); Mads Olsen, Kobenhavn S (DK)

(73) Assignee: Mindmetric Ltd., London (GB)

( * ) Notice: Subject to any disclaimer, the term of this patent is extended or adjusted under 35 U.S.C. 154(b) by 322 days.

(21) Appl. No.: 12/739,505

(22) PCT Filed: Oct. 23, 2008

(86) PCT No.: PCT/DK2008/050259
§ 371 (c)(1),
(2), (4) Date: Apr. 23, 2010

(87) PCT Pub. No.: WO2009/052833
PCT Pub. Date: Apr. 30, 2009

(65) Prior Publication Data
US 2012/0010474 A1      Jan. 12, 2012

(30) Foreign Application Priority Data

Oct. 23, 2007 (DK) ................................. 2007 01522
Nov. 23, 2007 (DK) ................................. 2007 01672
Dec. 3, 2007 (DK) ................................. 2007 01721

(51) Int. Cl.
*G06Q 40/00* (2012.01)
(52) U.S. Cl.
USPC ........................................ 705/7.11; 705/7.42
(58) Field of Classification Search
USPC .......................................... 705/7, 7.11, 7.42
See application file for complete search history.

(56) References Cited

U.S. PATENT DOCUMENTS 3,034,500 A * 5/1962 Backster, Jr. ................. 600/547
(Continued)

FOREIGN PATENT DOCUMENTS

| WO | WO-9733515 A1 | 9/1997 |
| WO | WO 99/59470 | 11/1999 |
| WO | WO-03065893 A1 | 8/2003 |

*Primary Examiner* — Thomas Dixon
*Assistant Examiner* — Benjamin S Fields
(74) *Attorney, Agent, or Firm* — Gifford, Krass, Sprinkle, Anderson & Citkowski, P.C.

(57) ABSTRACT

The invention relates to a system and a method for analysing with a temporal resolution below 160 milliseconds at least one response of a test person to at least one input stimulus. At least one input stimulus is provided to the test person and data representing the test person's response to this provided at least one input stimulus is obtained. From these data, at least one induced response pattern is determined in an automatic manner and at least one induced response pattern is identified. Optionally, the response pattern is interpreted and at least one induced response indicator is identified. The identified at least one induced response pattern and/or and at least one induced response indicator are synchronized to the presented at least one input stimulus. The synchronized at least one input stimulus and the determined at least one response pattern and/or at least one response indicator are presented in the same display and/or stored on the same means for storing. A database unit allowing the at least one input stimulus and/or the identified at least one induced response pattern to be stored and/or retrieved and/or compared to input stimuli and/or identified induced response patterns from analyses performed on the same test person and/or other test persons. The means for automatically determining comprises means for automatically analyzing the obtained data to identify at least one induced response pattern, or at least one feature thereof.

26 Claims, 7 Drawing Sheets

(56) References Cited

U.S. PATENT DOCUMENTS

| | | | |
|---|---|---|---|
| 3,548,806 A * | 12/1970 | Fisher | 600/484 |
| 3,727,604 A * | 4/1973 | Sidwell et al. | 600/372 |
| 4,041,617 A * | 8/1977 | Hollander | 434/237 |
| 4,931,934 A * | 6/1990 | Snyder | 434/236 |
| 5,243,517 A * | 9/1993 | Schmidt et al. | 600/544 |
| 6,099,319 A * | 8/2000 | Zaltman et al. | 434/236 |
| 6,236,885 B1 * | 5/2001 | Hunter et al. | 600/545 |
| 6,276,885 B1 | 8/2001 | Yamanaka | |
| 6,289,234 B1 * | 9/2001 | Mueller | 600/410 |
| 6,292,688 B1 * | 9/2001 | Patton | 600/544 |
| 6,315,569 B1 * | 11/2001 | Zaltman | 434/236 |
| 6,585,521 B1 * | 7/2003 | Obrador | 434/236 |
| 6,688,890 B2 * | 2/2004 | von Buegner | 434/322 |
| 2002/0188217 A1 * | 12/2002 | Farwell | 600/544 |
| 2005/0177058 A1 * | 8/2005 | Sobell | 600/545 |
| 2009/0083129 A1 * | 3/2009 | Pradeep et al. | 705/10 |

* cited by examiner

METHOD, SYSTEM AND COMPUTER PROGRAM FOR AUTOMATED INTERPRETATION OF MEASUREMENTS IN RESPONSE TO STIMULI

FIELD OF INVENTION

The present invention relates to a pattern recognition tool for automatic and high temporal resolution testing of a person's response to certain sensorial stimuli. In particular, the invention relates to the frame-by-frame analysis of a person's response to audio-visual stimuli such as a video sequence.

BACKGROUND OF INVENTION

It is desirable to evaluate how test persons respond to a variety of stimuli including, but not limited to, advertising commercials, TV shows, cinema movies computer games, TV games, internet, speeches, price information, audio-visual presentations in general, touch/feel, taste and smell. It has become increasingly clear that our emotional response to stimuli is autonomous and that the test persons only become aware of their response up to a full second after their brain have received the stimuli, if at all. In market and other research it is of great value to obtain data that is biologically objective and free from the test person's subjective interpretation.

The fact remains that today the most common measure or way of testing certain stimuli is by conducting introspective analysis (ask) or monitor what the test person does (see). There is a need for a tool, which enables developers of audio-visual and other stimuli to measure, in a cost effective manner, the objective biometric response to these stimuli. Attempts are being made with measuring pupil dilation, muscle movement and other measures, but these are only used to measuring a fraction of possible autonomous responses and cannot give an understanding of memory processes in the brain. Brain activity measurement techniques such as EEG, fMRI and others can.

Brain activity measures have been performed regularly for several years by now, but they are costly, labour intensive and complicated to perform. This is especially the case when a high temporal resolution is required for the analysis of video sequences, where the response to a large number of frames needs to be analyzed.

In order to be able to produce and adjust stimuli, such as audio-visual stimuli, to provide stimuli with a high impact and/or acceptance among persons exposed to the stimuli, the developers of the stimuli must be able to identify precisely which part(s) of the stimuli, such as a single frame in a video sequence, that induces a desired response in the test person. These responses relate to but are not limited to interpretations regarding the test person's attention level, his preferences (positive, neutral or negative), memory activation (working or long-term) and intention of action.

Schmidt et al. describes in U.S. Pat. No. 5,243,517 a method for automatically evaluating the emotional response of a test person to stimuli, such as a movie sequence for advertisement purposes. EEG signals measured on the test person are analyzed by a signal analyzing computer and information regarding the intent to buy and the memory of the product is derived by a two-step method, wherein the test person must view the video sequence twice, in order to provide the measurement of the response. The temporal resolution of the method according to U.S. Pat. No. 5,243,517 is in the order of seconds and this method hence provides a measurement of the average of the test person's response during this time.

Hunter et al. describes in U.S. Pat. No. 6,236,885 a system for synchronising the response of the test individual to a certain stimuli with the stimuli itself. The stimuli and the measuring components of the system are synchronized and controlled automatically to provide precise synchronization.

The above technologies primarily work on the central nervous system. However, in addition to the above other supportive measures can be made on the somatic and autonomic nervous systems supporting the findings from the analysis on the central nervous system. In some cases the analysis made on the somatic and autonomic nervous system may stand alone.

SUMMARY OF THE INVENTION

The applicants of the present invention have recognised that the main obstacle for tools capable of performing an analysis with a high temporal resolution of a test persons brain activity response to a certain sensorial stimuli becoming widespread in market research, such as evaluating TV commercials, the appeal of games, music, film, TV shows and other forms of entertainment, research and even some psychological evaluation, is the limited availability of neuroscientist to interpret the data and the cost of performing the analysis of the measurements. Especially in the case of high temporal resolution analysis, where e.g. the brain activity response to several frames each second must be analyzed, the task of performing the analysis is overwhelming. For this reason it would be desirable if biometric data and especially brain activity measures such as EEG data could be interpreted automatically in a manner that provides a high temporal resolution.

Accordingly, one object of the invention is hence to provide a system for analysing with a temporal resolution below 160 milliseconds at least one response of a test person to at least one input stimulus, comprising:
  a. means for providing the at least one input stimulus to the test person,
  b. means for obtaining data representing the test person's response to the provided at least one input stimulus,
  c. means for automatically determining at least one induced response pattern,
  d. means for synchronizing the identified at least one induced response pattern to the provided at least one input stimulus,
  e. means for presenting in the same display and/or means for storing on the same storage device the synchronized at least one input stimulus and the determined at least one response pattern,
  f. a database unit allowing the at least one input stimulus and/or the identified at least one induced response pattern to be stored and/or retrieved and/or compared to input stimuli and/or identified induced response patterns from analyses performed on the same test person and/or other test persons, wherein the means for automatically determining comprises means for automatically analyzing the obtained data to identify at least one induced response pattern, or at least one feature thereof.

A second object the invention relates to a method for analysing with a temporal resolution below 160 milliseconds at least one response of a test person to at least one input stimulus, comprising the steps of:

a. providing the at least one input stimulus to the test person,
b. obtaining data representing the test person's response to the provided at least one input stimulus,
c. automatically determining at least one induced response pattern,
d. synchronising the determined at least one induced response pattern, with the provided at least one input stimulus,
e. presenting in the same display and/or storing on the same storage device the synchronized at least one input stimulus and the determined at least one induced response pattern, wherein the step of automatically determining comprises automatically analyzing the obtained data to identify at least one induced response pattern, or at least one feature thereof.

A third object of the invention is a computer program product for analysing with a temporal resolution below 160 milliseconds at least one response of a test person to at least one input stimulus, comprising:

a. control of means configured to provide the at least one input stimulus to the test person,
b. control of means for obtaining data representing the test person's response to the provided at least one input stimulus,
c. control of means for determining at least one response pattern and/or at least one response indicator from the obtained data representing the test person response to said at least one stimuli,
d. control of synchronization of the determined at least one response pattern and/or at least one response indicator with the provide the at least one input stimulus,
e. control of presenting the determined at least one response pattern and/or at least one response indicator and the provide the at least one input stimulus in synchronization,
f. control of a database unit allowing the at least one input stimulus and/or the identified at least one induced response pattern and/or the identified at least one induced response indicator to be stored and/or retrieved and/or compared to input stimuli and/or identified induced response patterns and/or the identified induced response indicators from analyses performed on the same test person and/or other test persons.

A fourth object of the invention is to provide a pattern recognition tool comprising means for providing sensorial stimuli to a person, means for measuring the response, means for automatically analyzing and automatically interpreting the response, and means for presenting the stimuli and the response and/or interpretation in a synchronised and/or overlapping manner so that a person's response to for instance a video sequence can be evaluated with frame-to-frame precision.

Yet another object of the invention is to provide a system which collects data in such a way that synchronised data from several test persons can be analysed, interpreted, combined, averaged and displayed at the same time. The data from the several test persons may represent the response of these persons to the same stimuli. The interpretation of the data from several test persons to the same stimuli can be combined, averaged and used in a feedback-loop to improve the presentation of the stimuli.

Yet another object of the invention is to provide a system for developers of audio-visual and other stimuli, which provides easy and efficient editing or improvement of the stimuli along the lines of, but not limited to, attention, preference, memory and intention of action. The developers may be advertisers, game developers, moviemakers and others developers of stimuli. The developers can accurately adjust the stimuli according to the brain activity response of the test persons, be it on an individual or on a group basis. The response of the test persons can be used in a feedback loop to influence and change the stimuli later on while presented. A further object of the present invention is to present the stimuli and the test person's response to the stimuli in such a manner that the developer of the stimuli can use this to interpret and/or adjust the stimuli depending on the response desired. It is foreseen as relevant to be able to compare the results from brain activity responses on one set of stimuli to that of another set of stimuli from a similar category.

Another object of the invention is to provide a system that performs mind reading by automatically interpreting brain activity measures from test persons exposed to certain stimuli and presenting this interpretation alone or together with the provided stimuli on a monitor, storage device, paper or other format. A test person receives sensorial stimuli from a source, such as loudspeakers, a monitor or other stimuli from other sources, while the brain activity response to the provided stimuli is measured. This measurement is sent to a processor and compared to known brain activity responses stored in a database or algorithmically encoded. In this manner, the processor can establish values for measures such as attention, liking, memory and action among others by comparing the measured activity to a standard neuro-paradigm in the computer database. The analysis of data and the stimuli is then presented on a monitor or other formats.

Yet another object of the invention is to provide a novel system, which ensures a higher impact and/or acceptance of a provided stimuli by engaging the nervous systems in the most efficient way, by providing knowledge about the test person's attention level, his preferences (positive, neutral or negative), memory activation (working or long-term) and intention of action to enable the developers of stimuli such as audio-visual and other stimuli to adjust the stimuli according to the response of the test persons.

Yet another object of the invention is hence to automate the interpretation of nervous system response data, including, but not limited to brain response data, thus making it less costly and less complicated.

In a preferred embodiment of the invention the data obtained from the test person is stored in a database. Thus, the data relating to each test person is stored, i.e. the input stimulus, the data representing the test person's response, the data representing the response pattern and/or the data representing the response indicator(s) are stored in a database. This database preferably comprises response data from a plurality of test persons, thus the database is preferably incrementally updated with response data from test persons being exposed to the at least one input stimulus. In one embodiment individual data and/or demographic data for the test persons is stored in the database along with the response data.

In one embodiment of the invention typical response patterns and/or response indicators can be calculated based on the data in the database and with incrementally updated data typical response pattern(s) and/or typical response indicator(s) can be continuously calculated from the response data. This can preferably be provided by means of an adaptive algorithm, whereby a self-learning system can be provided. Thus the system can continuously adapt to the updated response data and thereby improve the ability to predict and/or recognize response patterns from the test persons. This can preferably be combined with individual and/or demographic data of the test persons, thereby providing a multifaceted adaptation to response patterns from test persons of for example different gender, age, nationality, educational level, habits and/or the like. Thus, according to one embodiment of the invention at least one typical response pattern and/or at least one typical response indicator calculated from the response data in the database represent at least one specific emotional response such as attention, liking, memory and/or intention of action.

One embodiment of the invention relates to the automatic analysis of a single test person. However, in yet another embodiment of the invention a system and a method is provided for analysing the response of a plurality of test persons to at least one input stimulus whereby the response of each of the test persons are analysed according to any of the methods described.

Each test person must be provided with the at least one input stimulus. This can for example be provided by distributing a video/audio signal to the test persons trough a communication network such as the internet. The distribution of the input stimulus does not have to be simultaneous to the test persons, but can for example be provided by means of the test persons requesting it, for example from a web server. Each test person must also be provided with means for obtaining the data representing the response to the stimulus. This can for example be one or more electrodes and/or a helmet registering one or more reactions in the various nervous systems of each test person, e.g. brain activity, perspiration, heart rate, respiration, temperature, eye movements, muscle activity, and/or the like. The data representing the response of each person must then be returned to the provider. This redistribution can for example be provided through the same communication network. In one embodiment response data is collected at the location of each test person and subsequently returned, in another embodiment the response data is returned instantly and live. In any case the response pattern determined from the response data must be synchronized with the input stimulus. The response data from each test person is preferably provided to at least one central database. The test persons do not need to be in the same location. They can be separated in different rooms, buildings or even geographically separated in different cities, countries or continents. Input stimulus is distributed to the test persons, preferably by request, and response data is returned to the central database. The central database preferably also comprises information of individual and/or demographic data for the test persons.

The invention furthermore includes a computer program product having a computer readable medium, said computer program product comprising means for carrying out any of the methods listed herein.

DEFINITIONS

Figure 1:
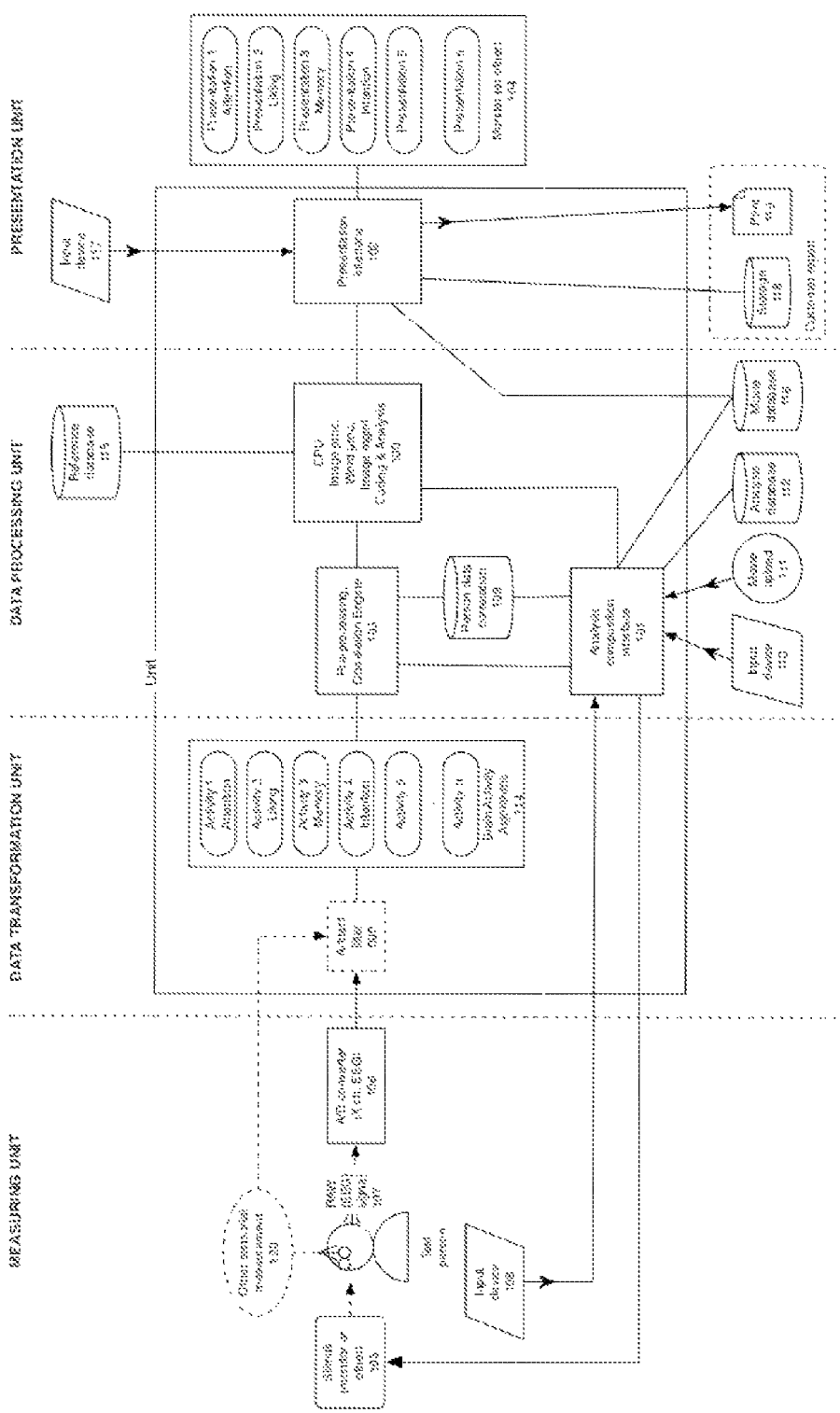
FIG. 1 illustrates the components of a preferred embodiment of the system.

As used herein stimuli refers to any sensory activation or combination of sensory activations be it audition, vision, gustation (taste), olfaction (smell), tactition (feel), chemoreceptive, photoreceptive, proprioreceptive, mechanoreceptive, thermoreceptive, nociceptive or other.

As used herein neuro-paradigm and/or known brain activity response refers to activity in the brain that is known to occur in defined circumstance e.g., the EP P300 when shown a previously observed visual stimulus, N400, hemispherical lateration, frequency/amplitude patterns and other known responses A neuro-paradigm may be supported by measures from other parts of the nervous system measured by biometric techniques. These may for example include ECG, EDA, eye-tracking and other measures that can be used to give a deepened understanding of activity in the nervous system.

As used herein attention, liking, memory and action refers to examples of separate neuro-paradigms.

As used herein the neuro-paradigm action refers to evaluating the intention of performing an action based on the provided stimuli.

As used herein interpreted data refers to response signals that have been analysed, the known neuro-paradigms identified and the data has been time matched to the stimuli that caused the response.

As used herein EEG refers to any type of electro physiological measurement of brain activity.

As used herein EMG (electromyography) refers to evaluating and recording the activation signal of muscles. An electromyograph detects the electrical potential generated by muscle cells when these cells contract, and also when the cells are at rest.

As used herein Eye tracking is the process of measuring either the point of gaze ("where we are looking") or the motion of an eye relative to the head. An eye tracker is a device for measuring eye positions, eye movements and in some cases pupil dilation and eye blinks.

As used herein ECG refers to a noninvasive measure of the electrical activity of the heart over time. The heart rate can for example be deduced from an ECG signal, but a variety of parameters can be calculated from this measure. Heart rate variability is commonly used to help evaluate valence measures.

As used herein GSR broadly refers to measuring electrodermal response. Other terms such as skin conductance response (SCR), EDR and EDA may also be used to describe this measure.

As used herein demographic data can comprise information about age, income, mobility, education, cultural background, employment status and the like. "Demographics" is a short term for population characteristics. A demographic segment is a group of a population with common demographic data.

As used herein individual data of a test person comprises information about gender (sex), age, various physical characteristics, diseases, genotype, ethnicity, habits, handedness, cognitive measures, educational level and/or the like. Information on habits can be information on smoking habits, physical activity, eating habits and/or the like. Many of these data types can also be termed demographic variables and/or population specific values.

A test person's response to certain stimuli may depend on his/her demographic variables or individual data. For example a test person's response to a specific image may depend on the educational level, nationality, age and the like. Thus, when analyzing the response from a test person a trustworthy correction for the expected response can be provided by knowing individual and/or demographic data for said test person.

The individual and demographic data for the test person(s) used involved in this invention can be any combination of the previously mentioned data types. In some cases it is only necessary to include a few individual data types, thereby simplifying the analysis.

Synchronisation

Measurement and data processing of reactions in the various nervous systems is a cumbersome process and in particular automatic measurement, registration and processing of emotions and emotional reactions are today quite unreliable. An object of the present invention is therefore to increase the reliability of automatic processing of data relating to emotional reactions, such as mind reading.

Precise synchronisation of the measured response data with input stimuli is a pivotal point in this invention. This is crucial to precisely determine a person's reaction to a specific stimulus, for example in a series of stimuli. One such preferred synchronisation method when audiovisual stimuli are presented to the test subject is to emit a PCM or similarly encoded sound that is by means of a microphone or a cable picked up by the electronic equipment that captures data from the test subject. This is similar to the use of a clapperboard in movie production to synchronise sound and picture as well as to identify the individual takes.

Another aspect of synchronisation is the calibration of the individual test subject, i.e. different persons react differently to the same stimulus. For example in terms of how the reaction is embodied and how fast the reaction happens. These issues can be addressed by calibrating each test subject, for example by measuring the reaction to specific, possibly simple, stimuli in a calibration sequence.

When multiple persons are subject to emotional response test, possibly concurrently, a substantial amount of data is aggregated and once again synchronisation is essential. In a preferred embodiment of the invention data are normalised prior to aggregation. For example response data and/or response patterns are normalised in term of biological individual data and/or non-biological demographic data. Data can be normalised for each test subject and/or for groups of test persons, such as groups with common individual and/or demographic data.

In a further embodiment of the invention time varying confidence values, sometimes called quality attributes, can be assigned to one or multiple series of response data, for example in terms of an individual test subject, for the purpose of improving the data aggregation process. For example the interpretation values for attention and liking could be deemed unreliable for an individual A in the beginning of a movie and reliable in the middle, whereas for individual B the values for liking could be deemed reliable all the time and the values for attention unreliable in the end, 40% reliable in the middle and fully reliable in the beginning. The aggregation process could take this into account for example by simple weighing of the attention and liking values or by more sophisticated means.

In one embodiment of the invention multiple biometric sources are provided to obtain multiple data series, i.e. at least one data series from each biometric source. Interpreting these data series is a question of isolating individual components of biological responses from data that are overlaid in additive or other more complicated ways. Each biometric source will most likely have its own characteristic profile with respect to event related responses, for example in terms of latency, amplitude, recovery rate, conditioning and the like. It is crucial to address how responses combine when they are overlaid because of events that occur timewise too close for one response to fully end before the next begins.

Thus, with the use of multiple biometric sources synchronisation is pivotal in terms of identifying which stimulus caused which biological response. However, knowing the characteristic response profile of each biometric source can help mathematically identifying and separating multiple overlaid responses, such as those that can occur when stimuli vary quickly, as it is for example the case in movies. Thus, when a test person is only monitored by means of a single biometric source, synchronisation to each single stimulus can be difficult when stimuli vary quickly. However, if the test person is equipped with more than one biometric source the overlay of the different biometric response signals can provide a better identification and synchronisation of each stimulus.

The biometric response signals according to the invention are related to reactions in one, two or preferably three of the nervous systems: the central, somatic and the autonomous nervous system. This gives a variety of possible variations in response characteristics.

In a further embodiment of the invention measurements from both left and right side of the body test person are provided. This hemispherical asymmetry, such as with respect to lateration, can manifest itself even in measurements related to the somatic and the autonomous nervous system.

DETAILED DESCRIPTION OF THE INVENTION

FIG. 1 illustrates the components of a preferred embodiment of the system of the present invention used to automatically interpret a test person's response to certain stimuli. The applicants of the present invention anticipate widespread uses for such an automated mind reading system as in the present invention. One envisioned use of the system is not only to measure and interpret a person's level of attention, preference for, ability to memorise and intention for action, but to use the system to improve responses to audio-visual and other stimuli, such as advertisements, TV and computer games, movies, TV shows, speeches etc.

The system according to the present invention displays data both of the interpretation of the data and the stimuli. The recorded data can be displayed or replayed to evaluate the test person's reaction to the stimuli in a time-synchronised manner. In this manner the precise stimuli soliciting a known neuro-paradigm can be found with precision down to a fraction of a second. The current invention uses EEG measures as input, but other measures such as fMRI, PET, IR, GSR, EMG, ECG, eye tracking and/or others could be used, in particular the combination of more than one measure. As an example, when performing manually operated EEG based lie-detection the test person respond to a previously seen stimuli with a event related potential called P300 i.e., the test subject respond to a known stimuli (e.g. a picture of a crime scene) with a known neuro-paradigm (EP P300). In one embodiment of the present invention the test person responds with known neuro-paradigms, but to stimuli that is only later synchronised to match the interpretation of the test person's response.

Synchronisation is one of the pivotal points in this invention. The induced response pattern must be synchronized with the input stimulus, preferably on a millisecond level. Preferably all types of video-signals can be analysed, at least on a frame-to-frame level. In a preferred embodiment of the invention analysis can be provided multiple times for each frame of a video signal. Input stimulus can for example be video signals in all common broadcast standards can be analysed, such as HDTV, DVB-T, Mpeg2, Mpeg4, PAL, SECAM, NTSC and/or the like. According to the invention the mentioned broadcast video signals can all be synchronized to the response pattern, at least on a frame-to-frame basis.

Synchronisation is also important when test persons are subject to several measurements of the reaction of the various nervous systems. Coordinating the signal from two or more body activity indicators is not a simple task. Body activity signals like EEG, EMG, GSR, temperature, ECG, heart rate, blood pressure, eye movements. Some signals may provide a response on a millisecond level, like EEG, whereas others, like body temperature, can be slowly varying—on the order of minutes or even hours. However, by the system and method according to the invention each data (signal) representing response data from one body activity of a test person is analysed to determine at least one induced response pattern. And each induced response pattern originating from a specific body activity signal is preferably synchronized with the at least one input stimulus. Thus, even though the timing is different for different body activity signals, it is crucial to synchronize the different induced response patterns with the at least one input stimulus, to determine how the test person(s) react to specific events in the input stimulus.

In a preferred embodiment of the invention the timing of the response data from a test person can be measured during the calibration step. Response data from a plurality of test persons to the calibration is preferably stored on the database. Applying an adaptive algorithm to this data can help the system "learn" the timing and/or the response from test persons. The adaptive algorithm preferably takes into account individual and/or demographic data of the test persons, thereby over time acquiring information on the timing of response signals and/or how different test persons respond to certain stimuli. This can help synchronise the different response patterns with the input stimulus. An adaptive algorithm can also be provided to the data from the response data from the plurality of test persons, thereby also providing information of synchronisation of response signals and/or response patterns.

It is the vision that the test person is exposed to certain stimuli and that measurement(s) relating to activity in the nervous system(s), e.g. brain activity, of the test subject is made simultaneously. The brain activity can for example be measured in the form of EEG measurements, but perspiration, respiration, heart rate, eye movements, blood pressure, muscle activity and/or body temperature can also be measured as an indication of the test person's response to the stimuli.

The system then interprets these measurements by comparing them to known nervous system reactions for certain types of emotional responses such as Attention, Liking, Memory and intention of Action (ALMA). Based on this comparison the system can detect and interpret whether the stimuli demands the attention of the test subject, is liked or not liked, is stored in long-term memory or discarded and whether the test person displays the normal nervous system activity of a person with the intention of making an action. In this manner the system can, amongst others, evaluate precisely at which portion of the stimuli the test person was most engaged and at which portions the test person was least engaged without a person such as a neuro-scientist having to evaluate the data.

In the present invention, and the above-discussed example, the focus is on audio-visual stimuli. However, the display monitor could be replaced with other devices that would enable the system to interpret test person's responses to touch/feel, smell and taste. Regardless of the type of stimuli, brain activity data such as, but not limited to, EEG of the test person must be obtained. This data may or may not be correlated to other biometric measures.

The system according to the present innovation will now be described in greater technical detail by reference to FIG. 1. At the Measuring Unit of the system the test person's response to the stimuli is measured using standard EEG equipment or other types of equipment and the data is converted to computer format. The Data Transformation Unit initially controls and removes artefacts from the measurement that may impede interpretation and then compares the responses of the test subject to established neuro-paradigms or brain activity algorithms for interpretation. At the Data Processing Unit the stimuli is correlated or synchronised with the interpretation of the data from the test subject and an age related adjustment is made for the data to better reflect a standard brain. The analysis may be compared to other analysis prior to moving to presentation. In Presentation the interpretation of the measurement as well as the stimuli is presented according to the same time lines.

The test person uses the input device (108) to enter personal and/or individual data, such as sex, age, various physical characteristics, diseases, genotype, ethnicity, habits, handedness, cognitive measures, educational level and/or the like. Also demographic data relating to the test person may be entered. The analysis composition interface (101) displays stimuli that have been received from the input device (110) on the monitor (105). The raw EEG data (107) or other data are then measured and converted to digitalised computer format (120), but as some of the channels of the EEG measurement are assumed to be filled with artefacts these channels are removed from the observation (120/000). The signal then goes through a standard process of being a) de-trended in a high-pass filter, b) submitted to independent component analysis by temporal de-correlation, c) submitted to a short time Fourier analysis and d) concatenated to vectors. This process may or may not be amended with other calculation steps. Depending on the success rate the process of readying the data for interpretation may be modified. The result of this process is then related to the brain activity algorithms (114) stored on the computer for interpretation. One further step in an interpretation the data is to account of individual data, for example it is known that older test persons generally will display less activity than younger test persons. The pre-processing correlation engine (103) then compresses the interpretation of data from at least several hundred data points a second to for instance 25 a second in order to synchronise the interpretation of data with the actually stimuli given in 25 frames per second, like as is the case for a standard video signal. High quality/high definition video signals may comprise more than 25 frames per second, maybe for example 30 frames per second or even higher. Such high frame rates can also be synchronised to the input stimuli by the system and method according to the invention. The CPU (100) processes this data with other similar interpretations stored in the reference database (115) allowing for the test of several test persons to be subjected to statistical analysis and averaging. The results of the CPU (100) process is transferred to a presentation interface (102) that can receive further information regarding the test from the input device (117) and present these either in monitor format (104), print (119) or storage (118).

Figure 2:
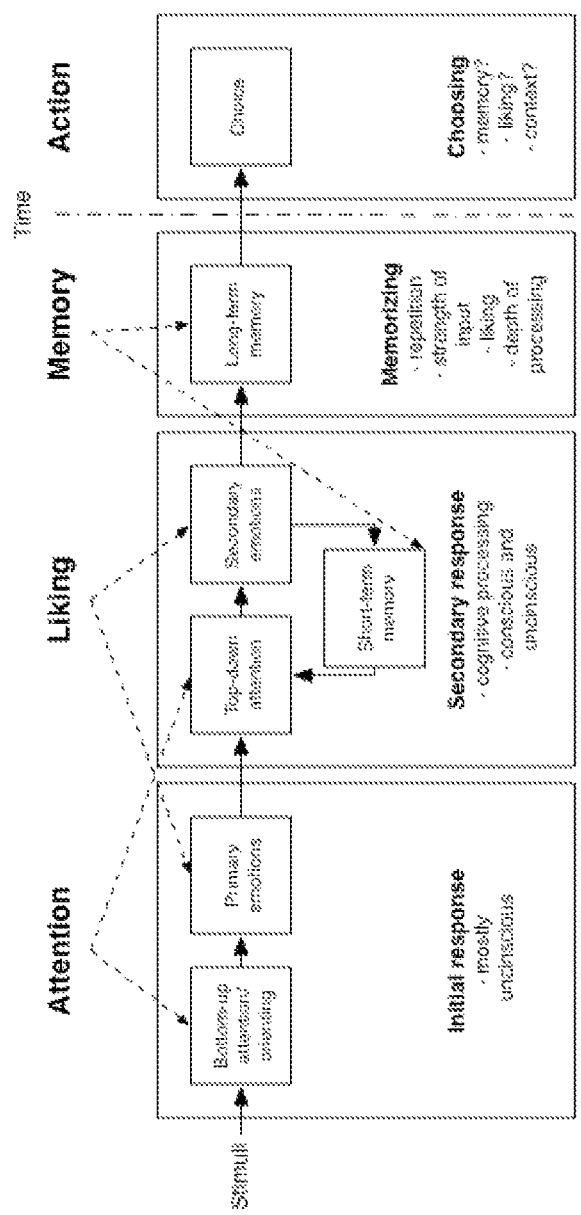
FIG. 2 illustrates the process of the invention from a user point of view.

FIG. 2 illustrates the process of the invention from a user point of view, whereby attention leads to preference building in the form of liking (or disliking), an emotional coding of the stimuli received influences whether or not the test person assign memory capacity to the stimuli and a combination of these factors decides whether the test person is likely or unlikely to act on the stimuli received.

Figure 3:
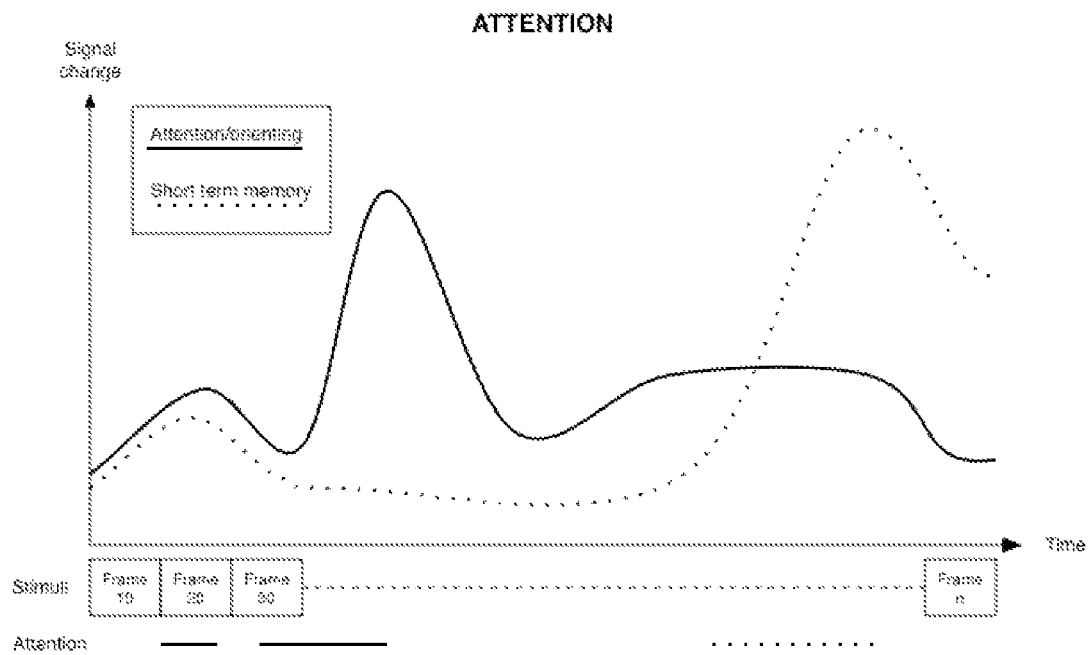
FIG. 3 illustrates a suggested outcome of the measurements analysed for attention.

FIG. 3 exemplifies a representation of the interpreted data in regards to attention and short term memory seen over the time period of the stimuli.

Figure 4:
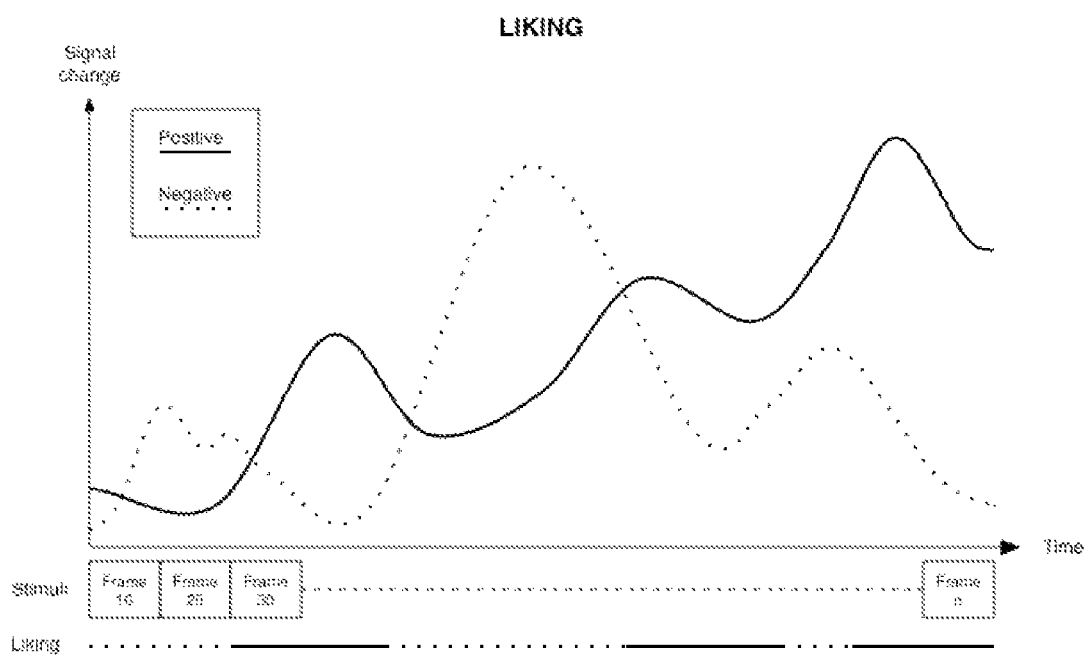
FIG. 4 illustrates a suggested outcome of the measurements analysed for liking.

FIG. 4 exemplifies a representation of the interpreted data in regards to liking seen over the time period of the stimuli.

Figure 5:
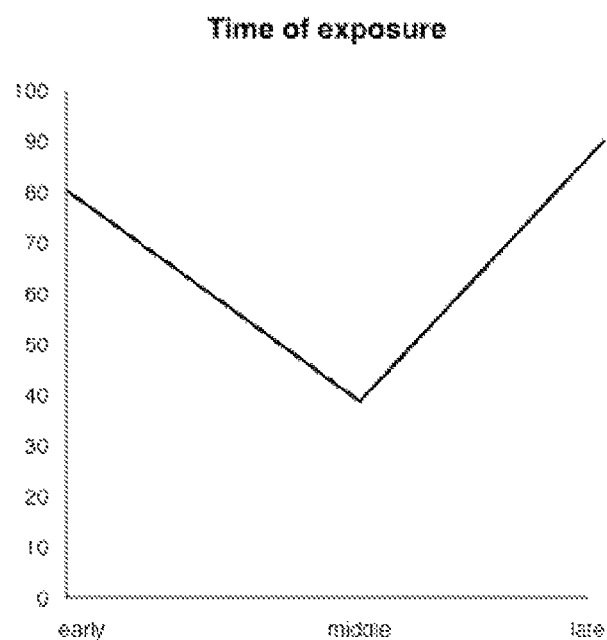
FIG. 5 illustrates a suggested outcome of the measurements analysed for memory.
Figure 5:
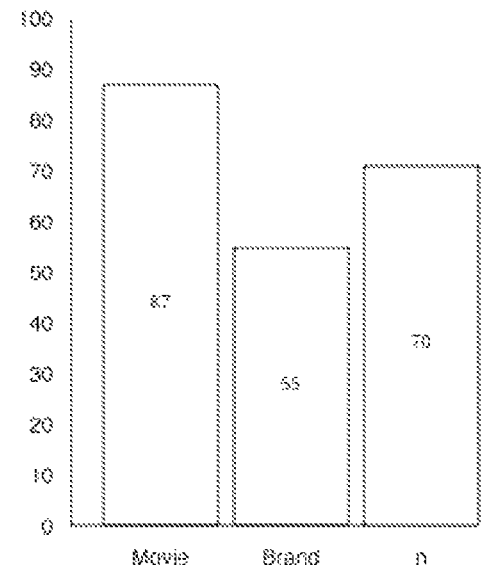

FIG. 5 exemplifies a representation of the interpreted data in regards to longer-term memory seen over the time period of the stimuli. The likelihood of an intention to act based on the stimuli is foreseen to be presented as a percentage figure.

Figure 6:
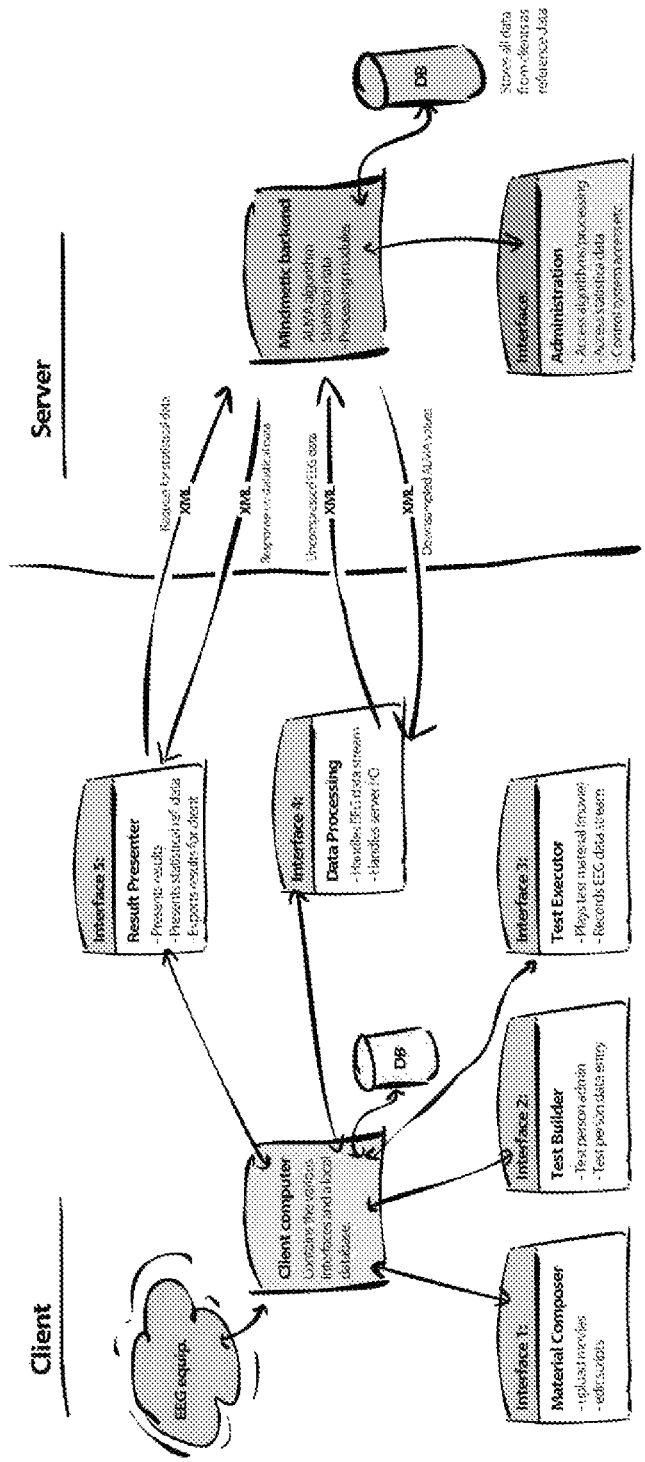
FIGS. 6-8 give a schematic presentation of some ASP based solutions of the system.
Figure 7:
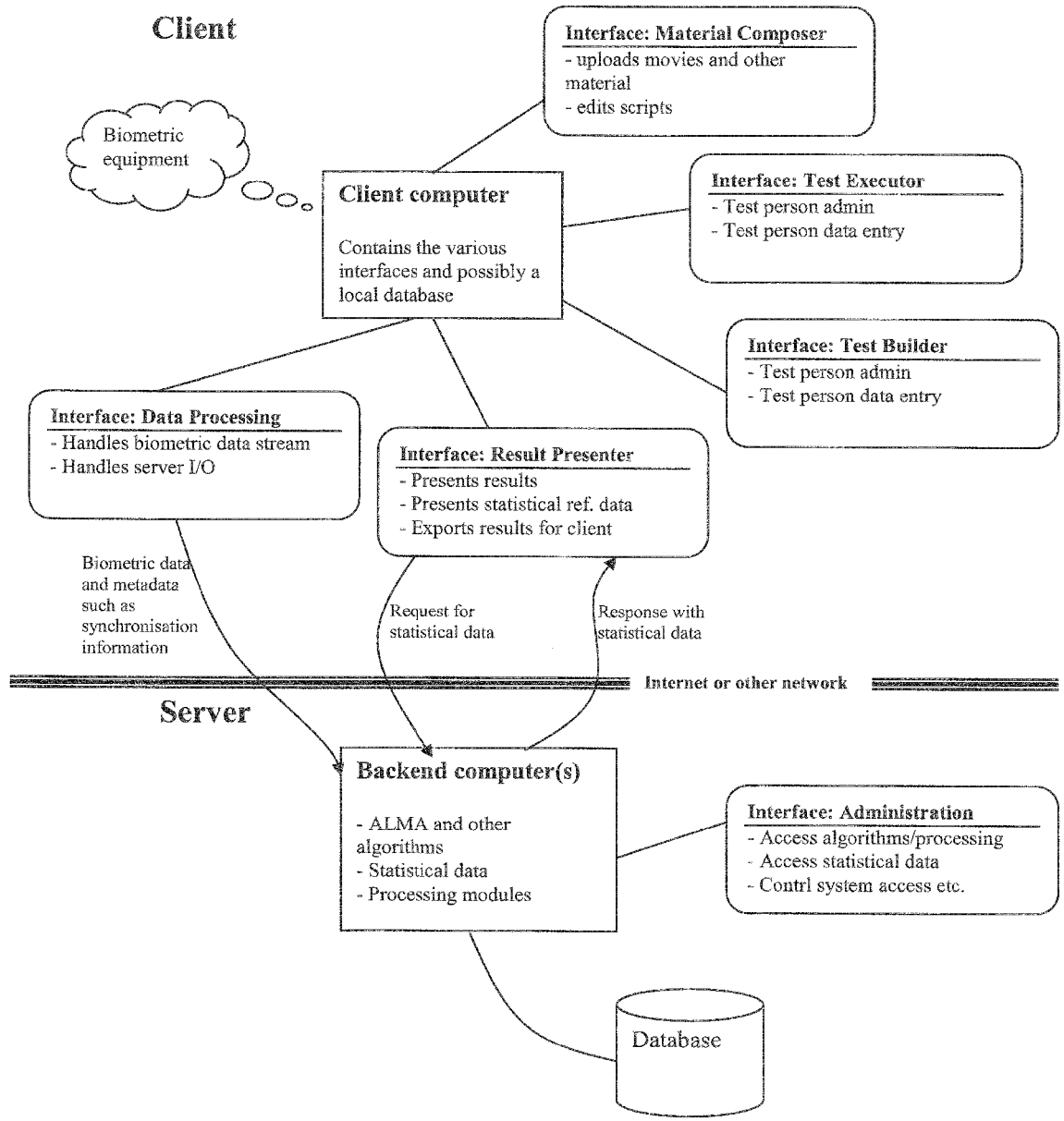
Figure 8:
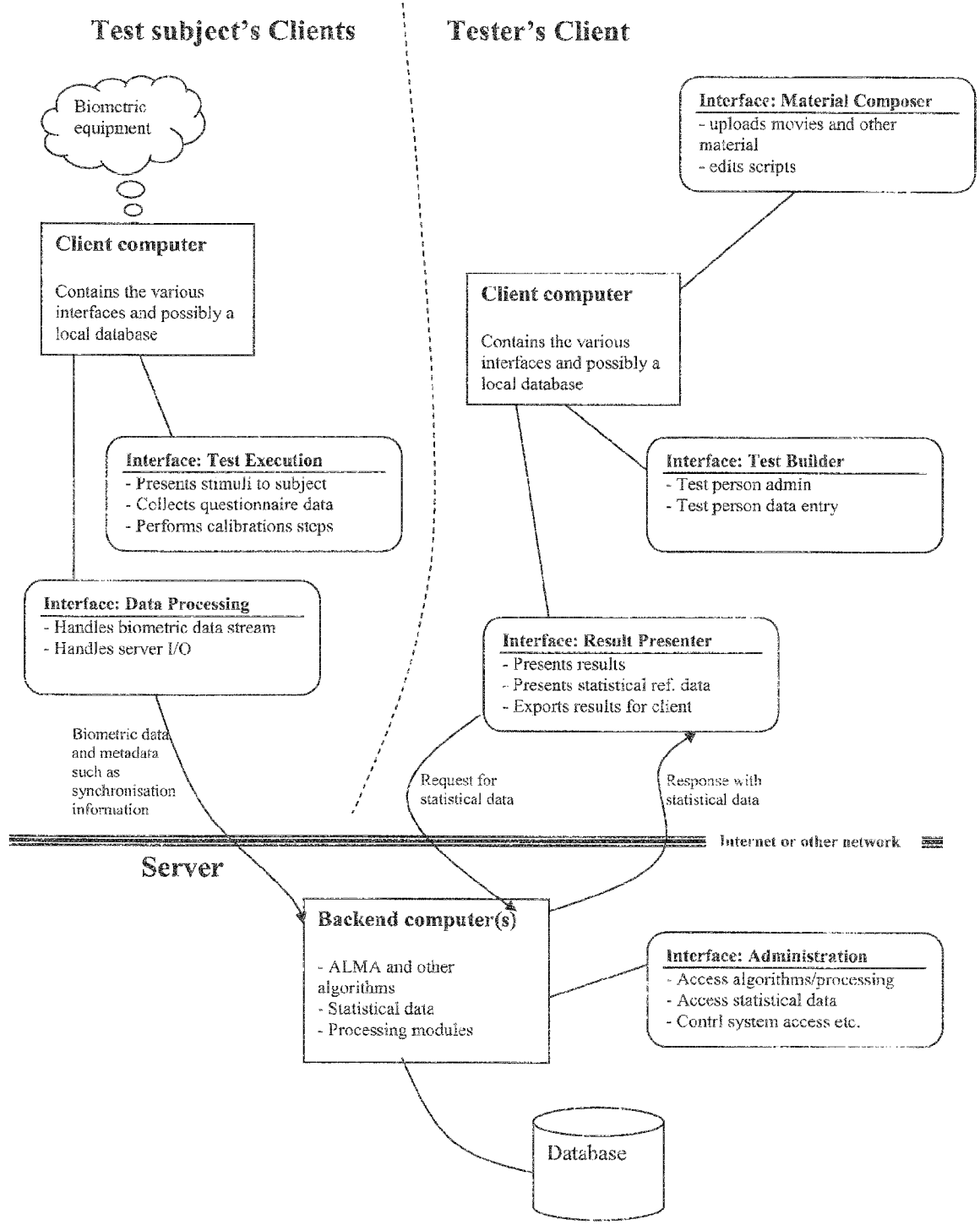

FIGS. 6, 7 and 8 illustrate solutions, where several features of the method and system according to the invention are moved to a remote location, such as central unit providing services for clients using the emotional pattern recognition tool. At the client site, a Client computer controls the biometric equipment, and interfaces for a material composer, a test builder, a test executor, data processing, and result presenter. In some embodiments test execution will be handled by a plurality of separate clients that do not contain any material composer, test builder, or result presenter. The material composer provides means for uploading the stimuli, such as video sequences or audio, and means for editing scripts. The test builder provides means for entering information relating to the test person, and the test executor provides the stimuli to the test person and records the biometric data stream. The biometric data stream and the server I/O is handled in the data processing interface. The results and statistical reference data are presented in the result presenter interface, where the results are exported for the client. The data processing interface and the result presenter interface are in communicative connection with a central server unit provided at a service provider's end. The algorithms for the analysis and interpretation of the biometric data are handled in this central unit, which also provides means for handling statistical data and the processing modules. A database unit is connected to the central server unit which also is connected to an administration interface. The administration interface provides means for accessing the algorithms/processing means, and the statistical data. Furthermore, the administration interface comprises means for controlling the system access. The communicative connection from the central server unit to the data processing interface and the result presenter interface located at the client's site is established by network connections, which transfers requests for statistical data from the central server unit and returns a response with statistical data to the result presenter interface. From the data processing interface response data are transferred to the central server unit which returns interpreted data, such as Attention, Liking, Memory and Action (ALMA) and other values determined by the central server unit. This approach offers several advantages to the service provider. First of all, he can accumulate knowledge from the client's test results and build an extensive database. Furthermore, he can sell individual and customized services such as processing and comparison with the extensive database of responses to a large variety of stimuli. The maintenance and improvement of the algorithms for the analysis and interpretation is also handled centrally and hence requires only limited effort compared to the situation where the individual clients are operating a system wherein all features are provided at the client sites.

A person operating the system will be able to choose in which of the above formats the presentation should be given, when entering the presentation mode in section (102) of FIG. 1. This platform likely contains technologies such as .NET, Flash and Flash video (FLV). Data gathering and processing can be provided by means of Microsoft.NET, ensuring high performance and availability of standard functionality. Data will preferably be stored in a SQL Server. Other technology platforms than the ones mentioned here may be used.

The presentation part can be provided by means of Adobe Flash-technology and possibly Adobe Flex/Adobe Air-technologies, which enables development of desktop applications. Flash is well suited for graphical interfaces. Furthermore, Flash is well suited for displaying vector-based graphs and for embedded video. Moving pictures will preferably be shown in Flash video (FLV format) and in a fixed format (height/width) as well as with a fixed frame rate. The video is preferably compressed ensuring time accurate start and play. It is to be foreseen that within a foreseeable time horizon other technologies than the ones mentioned here may be used to perform a similar task.

The method according to the invention is capable of analysing with a temporal resolution below 160 milliseconds at least one response of a test person to at least one input stimulus. At least one input stimulus is provided to the test person and data representing the test person's response to the provided at least one input stimulus is obtained. At least one induced response pattern is automatically determined and synchronised, with the provided at least one input stimulus. The synchronized at least one input stimulus and the determined at least one induced response pattern are presented in the same display and/or stored on the same storage device. The step of automatically determining comprises automatically analyzing the obtained data to identify at least one induced response pattern, or at least one feature thereof.

The method's step of automatically determining may furthermore comprise a step of automatically interpreting the identified at least one induced response pattern, or at least one feature thereof, to provide the at least one response indicator. Furthermore, the step of synchronizing may comprise synchronising the determined at least one response indicator, with the provided at least one input stimulus. In addition, the step of presenting may further comprise presenting in the same display and/or storing on the same storage device the synchronized at least one input stimulus and the determined at least one response indicator. The step of automatically interpreting may comprise comparing the identified at least one induced response pattern, or at least one feature thereof, to at least one known response pattern and/or least one known response indicator, which may be stored on a database In one embodiment, the obtained data representing the test person's response to the provided at least one input stimulus comprises data relating to the test person's brain activity, such as an electroencephalogram (EEG). Preferably, the person's response to said at least one input stimulus comprises at least one induced emotional response. In a preferred embodiment, the at least one induced response pattern and/or the at least one response indicator comprises at least one known neuroparadigm, such as the event related potential EP P300 and/or the event related potential N400.

In a preferred embodiment, the step of determining comprises the use of at least one algorithm, such as an algorithm for pattern recognition.

The method may comprise the analysis of the test person's response to the stimuli without making any comparison with results obtained from other test persons, or it may comprise a step for comparing the identified response pattern of the test person to that of other test persons.

The temporal resolution of the automatic method is below 160 milliseconds, more preferably below 125 milliseconds, more preferably below 100, milliseconds, more preferably below 75, milliseconds, more preferably below or equal to $\frac{1}{14}$ seconds, more preferably below or equal to 40 milliseconds, more preferably below or equal to 1/30 seconds, more preferably below 25 milliseconds, more preferably below 10 milliseconds, more preferably below 5 milliseconds, preferably below 1 milliseconds.

In a preferred embodiment, the method comprises a step of calibrating the test person's response. At least one calibration input stimulus is provided to the test person and the obtained data are analyzed and interpreted. The step of calibrating may further comprise indexing against a standardized database, thereby taking into account the difference in the response to stimuli in test persons of different sex and/or different age. Furthermore, the indexing may take account for test persons of different height, weight, genotype, nationality, ethnicity, habits, handedness and/or cognitive measures. Test persons from different demographic segments may also be accounted for in the indexing. During calibration the latency and/or strength of at least one response indicator is determined from the test person's response to at least one calibration stimuli, with a precision better than 50 milliseconds, preferably better than 40 milliseconds, preferably better than 30 milliseconds, preferably better than 20 milliseconds, preferably better than 10 milliseconds, preferably better than 5 milliseconds, preferably better than 1 milliseconds.

In a preferred embodiment, the at least one input stimulus comprises audio and/or video signals, such as a video signal for entertainment and/or promotional purpose. Preferably, the at least one response indicator determined from the test person's response to the video signal is determined on a frame-by-frame basis providing information relating to the test person's response to the individual frames of the video.

In a preferred embodiment, the method can be utilized for editing in a movie with frame-to-frame resolution.

A preferred embodiment of the invention relates to a system for analysing with a temporal resolution below 160 milliseconds at least one response of a test person to at least one input stimulus. The system comprises means for providing the at least one input stimulus to the test person, means for obtaining data representing the test person's response to the provided at least one input stimulus, means for automatically determining at least one induced response pattern, means for synchronizing the identified at least one induced response pattern to the provided at least one input stimulus, means for presenting in the same display and/or means for storing on the same storage device the synchronized at least one input stimulus and the determined at least one response pattern, and a database unit allowing the at least one input stimulus and/or the identified at least one induced response pattern to be stored and/or retrieved and/or compared to input stimuli and/or identified induced response patterns from analyses performed on the same test person and/or other test persons. The means for automatically determining comprises means for automatically analyzing the obtained data to identify at least one induced response pattern, or at least one feature thereof.

The system's means for automatically determining may furthermore comprise means for automatically interpreting the identified at least one induced response pattern, or at least one feature thereof, to provide the at least one response indicator, wherein the means for synchronizing further comprises means for synchronising the determined at least one response indicator, with the provided at least one input stimulus, and the means for presenting further comprises means for presenting in the same display and/or storing on the same storage device the synchronized at least one input stimulus and the determined at least one response indicator, and the database unit allowing the at least one input stimulus and/or the identified at least one induced response indicator to be stored and/or retrieved and/or compared to input stimuli and/or identified induced response indicator from analyses performed on the same test person and/or other test persons.

In a preferred embodiment of the system the means for automatically interpreting comprises means for comparing the identified at least one induced response pattern, or at least one feature thereof, to at least one known response pattern and/or least one known response indicator.

The means for providing at least one input stimulus comprise means for providing audio and/or video signals and/or other stimuli such as smell, taste and touch to the test person.

In a preferred embodiment, the system comprises means for obtaining data representing the test person's response to the provided at least one input stimulus comprises means for measuring the test person's brain activity, such as means for obtaining an electroencephalogram (EEG).

Preferably, the synchronizing means of the system comprises means for matching in time the at least one induced response pattern, or at least a feature thereof, to the at least one input stimulus in such a manner that the induced response pattern or the at least a feature thereof, can be interpreted regardless of the sex and age of the test person. Preferably, the synchronizing means of the system comprises means for matching in time the at least one determined response indicator to the at least one input stimulus in such a manner that the test person's response can be interpreted regardless of the sex and age of the test person. The means for synchronizing preferably comprises means for matching in time the at least one determined response indicator and/or the induced response pattern, or at least a feature thereof, to a specific stimuli that caused the response without the stimuli being precisely identifiable prior to the data interpretations.

Preferably, the means for determining and/or the means for synchronizing, comprises means for taking factors influencing the at least one determined response indicator and/or the induced response pattern, or at least a feature thereof, into account. Preferably these means comprises means based on standard measures for each sex and age group.

In a preferred embodiment, the system can be used to identify at least one induced response indicator and/or the at least one determined response indicator, which comprises at least one known neuro-paradigm, such as the event related potential EP P300 and/or the event related potential N400.

In yet another preferred embodiment, the system comprises means for presenting, which comprises means that enable the user of the invention to utilize the synchronised presentation of the stimuli and the interpreted brain activity response to advise, edit, improve and/or other related counselling on the stimuli subjected to testing.

Preferably, the system comprises analytical means, which comprises at least one algorithm, such as at least one algorithm for pattern recognition. The analytical means may furthermore comprise means for comparing the obtained data with calibration data from the test person obtained when he or she is provided with calibration stimuli.

In a preferred embodiment of the system, it comprises means for presentation that may enable the user of the invention to utilize the synchronised presentation of the stimuli and the interpreted response to advise, edit, improve and/or other related counselling on the stimuli subjected to testing.

Furthermore, the system may further comprise means for cleaning said obtained data to remove signal artefacts.

In a preferred embodiment, the invention relates to a computer program product for analysing with a temporal resolution below 160 milliseconds at least one response of a test person to at least one input stimulus. The computer program product may provide control of means configured to provide the at least one input stimulus to the test person, control of means for obtaining data representing the test person's response to the provided at least one input stimulus, control of means for determining at least one response pattern and/or at least one response indicator from the obtained data representing the test person response to said at least one stimuli, control of synchronization of the determined at least one response pattern and/or at least one response indicator with the provide the at least one input stimulus, control of presenting the determined at least one response pattern and/or at least one response indicator and the provide the at least one input stimulus in synchronization, control of a database unit allowing the at least one input stimulus and/or the identified at least one induced response pattern and/or the identified at least one induced response indicator to be stored and/or retrieved and/or compared to input stimuli and/or identified induced response patterns and/or the identified induced response indicators from analyses performed on the same test person and/or other test persons. Preferably, the computer program code includes a mechanism for the comparison of brain activity measures from a test person to known brain activity responses for the benefit of automatic interpretation of the brain activity measurement data.

In a preferred use to the invention, it is used for frame-by-frame analysis of nervous system response of a test person when at least one visual input stimulus is provided to the test person.

Galvanic skin response (GSR), also known as electrodermal response (EDR), psychogalvanic reflex (PGR), or skin conductance response (SCR), is a method of measuring the electrical resistance of the skin. There has been a long history of electrodermal activity research, most of it dealing with spontaneous fluctuations. Most investigators accept the phenomenon without understanding exactly what it means. There is a relationship between sympathetic activity and emotional arousal, although one cannot identify the specific emotion being elicited. The GSR is highly sensitive to emotions in some people. Fear, anger, startle response, orienting response and sexual feelings are all among the emotions which may produce similar GSR responses.

One branch of GSR explanation interprets GSR as an image of activity in certain parts of the body. The mapping of skin areas to internal organs is usually based on acupuncture points.

Obviously, numerous additional variations and modifications of the present invention are possible based on the above discussion. It is therefore to be understood that within the scope of the amended claims the invention may be practised otherwise than as specifically described herein.

EXAMPLES

The below examples are only meant as examples. Other test paradigms, other interpretations, other presentation formats and combinations with other test methods might be applied as well.

Example 1

A marketer wishes to test his new TV commercials prior to investing in airing the campaign. By testing the marketing stimuli on the invention the marketer obtains precise data on a test group response to this stimuli in terms of a) do they pay attention, b) do they like or dislike the material, C) is it memorized and d) is there a likelihood that the test group will respond with action to the given stimuli.

Based on the above information, the marketer will know the effect of the stimuli on a test group. The marketer can use the time accurate interpretation to edit the stimuli (e.g. remove sections that are not liked) in order to ensure that it has a higher impact. In this manner the marketer may have to spend less money airing the TV commercials, because the same effect can be achieved with a more effective commercial. Alternatively, the marketer can choose to increase the airing of the TV commercial if this is needed to ensure memorization.

In order to assist the marketer in making the above mentioned type of decision will make the average and fractal results of similar tests in similar industries available for benchmarking.

Example 2

In a manner similar to example 1, a moviemaker may wish to have an entire movie tested for attention, liking and other parameters and use the information and analysis obtained to edit the movie to be more attractive on the parameters defined.

Example 3

Similar to example 2, makers of TV film, TV shows, game shows and other audiovisual entertainment forms could have their productions tested prior to airing.

Example 4

In a manner similar to example one and two, Video or computer game producers can test new games for effectiveness using the present invention.

Example 5

In a manner similar to example 1, a musicians or music producer may wish to have music evaluated on specific parameters similar to the ones used in the above examples, allowing for the mixing of the sound material or music to be improved on liking and/or other parameters defined.

Example 6

A food manufacturer or other could test the response of test persons to the taste of new products, i.e. does it create a feeling of like or dislike.

Example 7

A perfume manufacturer could investigate new smells in a similar fashion to example 6.

Example 8

A clothing manufacturer could investigate the touch and feel of new fabrics vs. existing fabrics in a manner similar to example 6 and 7.

The invention claimed is:
1. A method for analyzing, with a temporal resolution below 160 milliseconds, at least one response of a test person to at least one input stimulus, comprising:
providing a computer server having a processor, a memory and a computer readable data storage medium;
providing an apparatus operable to measure a response of a test person to a input stimulus, the apparatus being in electronic communication with the computer server,
providing at least one input stimulus to a test person, obtaining by the apparatus data representing the test person's response to the provided at least one input stimulus and transmitting the obtained data to the computer server, automatically determining by the computer server at least one induced response pattern, synchronising by the computer server the determined at least one induced response pattern, with the provided at least one input stimulus, outputting by the computer server a data set including the synchronized at least one input stimulus and the determined at least one induced response pattern, wherein the step of automatically determining includes automatically analyzing the obtained data to identify at least one induced response pattern, or at least one feature thereof, and wherein the obtained data representing the test person's response to the provided at least one input stimulus includes data relating to the test person's brain activity, and wherein the method further includes calibrating the test person's response, the step of calibrating including analyzing and interpreting by the computer server the calibration data obtained when at least one calibration input stimulus is provided to the test person.

2. The method according to claim 1, wherein
a. the step of automatically determining further includes automatically interpreting the identified at least one induced response pattern, or at least one feature thereof, to provide at least one response indicator,
b. the step of synchronizing further includes synchronising the determined at least one response indicator, with the provided at least one input stimulus,
c. the step of outputting further includes presenting in the same display and/or storing on the same storage device the synchronized at least one input stimulus and the determined at least one response indicator.

3. The method according to claim 2, wherein the step of automatically interpreting includes comparing the identified at least one induced response pattern, or at least one feature thereof, to at least one of a known response pattern or least one known response indicator.

4. The method according to claim 2, wherein the at least one input stimulus, the data representing the test person's response, data representing the response pattern and/or data representing the response indicator are stored on a database in electronic communication with the computer server, wherein said database includes data from a plurality of test persons related to data representing the response, and/or data the representing pattern and/or data representing the response indicator.

5. The method according to claim 1, wherein at least one typical response pattern and/or at least one typical response indicator is continuously calculated based on data in the database an adaptive algorithm.

6. The method according to claim 1, wherein the at least one known response pattern and/or the at least one known response indicator and/or the at least one typical response pattern and/or the at least one typical response indicator represent at least one specific emotional response related to attention, and/or liking, and/or memory and/or intention of action.

7. The method according to claim 5, wherein the step of automatically interpreting includes comparing the identified at least one induced response pattern, or at least one feature thereof, to the at least one typical response pattern and/or the at least one typical response indicator.

8. The method according to claim 1, wherein the measured response relates to at least one of the central nervous system, the somatic nervous system and the autonomous nervous system.

9. The method according claim 1, wherein the obtained data representing the test person's response to the provided at least one input stimulus includes data relating to muscle activity of the test person.

10. The method according to claim 1, wherein the obtained data representing the test person's response to the provided at least one input stimulus includes data relating to the electrical activity of the heart and/or the heart rate of the test person.

11. The method according to claim 1, wherein the obtained data representing the test person's response to the provided at least one input stimulus includes data relating to the electrical resistance of the skin of the test person.

12. The method according to claim 1, wherein the obtained data representing the test person's response to the provided at least one input stimulus includes data relating to the position and/or movements of at least one of the test person's eyes, and/or pupil dilation and/or eye-blink.

13. The method according to claim 1, wherein the step of automatically determining includes determining at least one induced response pattern, or at least one feature thereof, by means of analyzing the data representing the test person's response relates to at least one of an EEG response signal, an EMG response signal, a GSR response signal, an Eye-tracking response signal and an ECG response signal.

14. The method according to claim 1, wherein the step of synchronizing further includes synchronizing the determined at least one induced response pattern and/or the at least one response indicator with the provided at least one input stimulus, and synchronizing of at least one of an EEG response signal, an EMG response signal, a GSR response signal, an Eye-tracking response signal and an ECG response signal 15. The method according to claim 1, wherein the at least one induced response pattern and/or the at least one response indicator includes at least one known neuro-paradigm.

16. The method according to claim 1, further comprising comparing the identified response pattern of the test person to that of other test persons.

17. The method according to claim 1, wherein the temporal resolution is below 50 milliseconds.

18. The method according to claim 1, wherein the step of calibrating comprises:
indexing against a standardized database,
determining the latency and/or strength of at least one response indicator determined from the test person's response to at least one calibration stimuli, and/or determining latency of the at least one response indicator with a precision better than 50 milliseconds.

19. The method according to claim 1, wherein the at least one input stimulus includes at least one of an audio or video signal.

20. The method according to claim 19, wherein the at least one response indicator determined from the test person's response to the video signal is determined on a frame-by-frame basis providing information relating to the test person's response to the individual frames of the video.

21. The method according to claim 4 wherein the plurality of test persons are physically separated and/or geographically separated.

22. The method according to claim 21, wherein the at least one stimulus and/or the data representing the responses are provided to and/or from the test persons through a communication network.

23. A system for analyzing, with a temporal resolution below 160 milliseconds, at least one response of a test person to at least one input stimulus, comprising:

provided a computer server having a processor, a memory and a computer readable data storage medium, the computer readable data storage medium including a database unit;

providing an apparatus operable to measure a response of a test person to a input stimulus, the apparatus being in electronic communication with the computer server, calibrating a test person's response to an input stimulus, providing at least one input stimulus to a test person, obtaining by the apparatus data representing the test person's response to the provided at least one input stimulus and transmitting the data to the computer server, automatically determining by the computer server at least one induced response pattern, synchronizing by the computer server the identified at least one induced response pattern to the provided at least one input stimulus, outputting by the computer server a data set including the synchronized at least one input stimulus and the determined at least one response pattern, the database unit operating to permit the at least one input stimulus and/or the identified at least one induced response pattern to be stored and/or retrieved and/or compared to input stimuli and/or identified induced response patterns from analyses performed on the same test person and/or other test persons, wherein the step of automatically determining includes automatically analyzing by the computer server the obtained data to identify at least one induced response pattern, or at least one feature thereof, and wherein the obtained data representing the test person's response to the provided at least one input stimulus includes data relating to the test person's brain activity, and wherein the automatically analyzing includes comparing the obtained data with calibration data from the test person obtained when the test person is provided with calibration stimuli.

24. The system according to claim 21, wherein a. the step of automatically determining further includes automatically interpreting by the computer the identified at least one induced response pattern, or at least one feature thereof, to provide the at least one response indicator, b. the step of synchronizing further includes synchronizing by the computer the determined at least one response indicator, with the provided at least one input stimulus, c. the step of outputting further includes presenting by the computer in the same display and/or storing on the same storage device the synchronized at least one input stimulus and the determined at least one response indicator, and d. the database unit allowing the at least one input stimulus and/or the identified at least one induced response indicator to be stored and/or retrieved and/or compared to input stimuli and/or identified induced response indicator from analyses performed on the same test person and/or other test persons.

25. A method for analyzing, with a temporal resolution below 160 milliseconds at least one response of a test person to at least one input stimulus, comprising:

providing a computer server having a processor, a memory and a computer readable data storage medium, the computer readable data storage medium including a database unit;

providing an apparatus operable to measure a response of a test person to a input stimulus, the apparatus being in electronic communication with the computer server, calibrating a test person's response to an input stimulus, providing at least one input stimulus to the test person, obtaining by the apparatus data representing the test person's response to the provided at least one input stimulus and transmitting the data to the computer server, determining by the computer server at least one a response pattern or a response indicator from the obtained data representing the test person response to said at least one stimuli, synchronizing by the computer server the at least one response pattern or at least one response indicator with the provide the at least one input stimulus, providing a database unit in electronic communication with the computer service, the database unit allowing the at least one input stimulus and/or the identified at least one induced response pattern and/or the identified at least one induced response indicator to be at least one of stored, retrieved, or compared to input stimuli and/or identified induced response patterns and/or the identified induced response indicators from analyses performed on the same test person and/or other test persons, wherein the obtained data representing the test person's response to the provided at least one input stimulus includes data relating to the test person's brain activity, and wherein the automatically determining step includes comparing the obtained data with calibration data from the test person obtained when the test person is provided with calibration stimuli.

26. The use of a method according to claim 1 for frame-by-frame analysis of the brain activity response of a test person when at least one visual input stimulus includes a video stimulus provided to the test person.

* * * * *

UNITED STATES PATENT AND TRADEMARK OFFICE
CERTIFICATE OF CORRECTION

| | | |
|---|---|---|
| PATENT NO. | : 8,560,360 B2 | Page 1 of 2 |
| APPLICATION NO. | : 12/739505 | |
| DATED | : October 15, 2013 | |
| INVENTOR(S) | : Birger Jan Olsen et al. | |

It is certified that error appears in the above-identified patent and that said Letters Patent is hereby corrected as shown below:

On the title page:

Abstract item (57):

Line 1, Delete "analysing", Insert --analyzing--

In the claims:

At column 17, claim number 1, line number 7, Delete "synchronising", Insert --synchronizing--

At column 17, claim number 2, line number 31, Delete "synchronising", Insert --synchronizing--

At column 17, claim number 3, line number 41, After or, Insert --at--

At column 17, claim number 4, line number 49, After and/or data, Delete "the"

At column 17, claim number 5, line number 55, After base, Insert --using--

At column 18, claim number 9, line number 5, After according, Insert --to--

At column 19, claim number 23, line number 9, Delete "a", Insert --an--

At column 20, claim number 25, line number 17, Delete "a", Insert --an--

At column 20, claim number 25, line number 24, After one, Delete "a"

Signed and Sealed this
Twelfth Day of May, 2015

Michelle K. Lee
*Director of the United States Patent and Trademark Office*

CERTIFICATE OF CORRECTION (continued)
U.S. Pat. No. 8,560,360 B2

At column 20, claim number 25, line number 30, Delete "provide", Insert --provided--

At column 20, claim number 25, line number 30, After provide, Delete "the"

At column 20, claim number 25, line number 32, Delete "service", Insert --server--